United States Patent
Chapman et al.

(10) Patent No.: US 12,092,619 B2
(45) Date of Patent: Sep. 17, 2024

(54) METHODS, MEDIUMS, AND SYSTEMS FOR LINKING CHROMATOGRAPHY DATA AND METADATA TO COMPLIANCE RISKS

(71) Applicant: Waters Technologies Ireland Limited, Dublin (IE)

(72) Inventors: Richard Chapman, Westborough, MA (US); Simon Meffan-Main, Manchester (GB); Tracy Hibbs, Nashville, TN (US)

(73) Assignee: Waters Technologies Ireland Limited, Dublin (IE)

( * ) Notice: Subject to any disclaimer, the term of this patent is extended or adjusted under 35 U.S.C. 154(b) by 118 days.

(21) Appl. No.: 17/716,696

(22) Filed: Apr. 8, 2022

(65) Prior Publication Data
US 2022/0326193 A1  Oct. 13, 2022

Related U.S. Application Data

(60) Provisional application No. 63/172,953, filed on Apr. 9, 2021.

(51) Int. Cl.
*G01N 30/88* (2006.01)
*G01N 30/06* (2006.01)
(Continued)

(52) U.S. Cl.
CPC ............. *G01N 30/16* (2013.01); *G01N 30/06* (2013.01); *G01N 30/64* (2013.01);
(Continued)

(58) Field of Classification Search
CPC ........... G01N 30/8658; G01N 30/8693; G01N 30/8696
See application file for complete search history.

(56) References Cited

U.S. PATENT DOCUMENTS 11,209,810 B2   12/2021   Wang et al.
2014/0303922 A1   10/2014   Manfredi
(Continued)

OTHER PUBLICATIONS

International Search Report and Written Opinion for International Patent Application No. PCT/IB2022/053333, mailed Jun. 28, 2022.
(Continued)

*Primary Examiner* — Jamel E Williams
*Assistant Examiner* — Alex T Devito
(74) *Attorney, Agent, or Firm* — Goodwin Procter LLP

(57) ABSTRACT

Exemplary embodiments provide methods, mediums, and systems for visualization and advanced data science on information collected in an analytical data system. Embodiments identify correlations and patterns in chromatography metadata around areas of potential user error. Correlations between these data sources may point to compliance risk areas. Metadata from the analytical system may be combined with other data sources and/or analytical data to correlate an analytical outcome with compliance artifacts. Supervised and/or unsupervised machine learning techniques may be used to combine these data source and learn correlations between them and compliance risks. The results of these analyses may be displayed on a dashboard, allowing a user to visualize compliance risks across an entire enterprise or supply chain. Automatic notifications of compliance risks may be generated and presented on a user interface. A system may also use pattern recognition to provide insights around potential compliance risks that have not yet occurred.

17 Claims, 14 Drawing Sheets

(51) Int. Cl.
    *G01N 30/16*     (2006.01)
    *G01N 30/64*     (2006.01)
    *G01N 30/86*     (2006.01)

(52) U.S. Cl.
    CPC ..... *G01N 30/8658* (2013.01); *G01N 30/8693* (2013.01); *G01N 30/8696* (2013.01)

(56) References Cited

U.S. PATENT DOCUMENTS

| | | |
|---|---|---|
| 2020/0379453 A1 | 12/2020 | Wang et al. |
| 2021/0190736 A1* | 6/2021 | Geiger ............... G01N 30/7233 |
| 2021/0325354 A1* | 10/2021 | Gugaliya ........... G01N 30/8624 |

OTHER PUBLICATIONS

International Preliminary Report on Patentability for International Patent Application No. PCT/IB2022/053333, mailed Oct. 19, 2023.

\* cited by examiner

Select Processing Page

Typhoon Data Explorer ▼

Upload file

Drag and drop file here
limit 200MB per file - 250N

[Browse files]

Select Data File example_typhoon_ms_inst_data_j___ ▼

Data Extraction

Scans ▼

Typhoon Data Explorer 0.0.2

File selected: example_typhoon_ms_inst_data.json

Overview

Overview | Warnings ⑩ | Reproduction

Warnings

- TDC has constant value '83204823 25889395'  [Constant]
- RP1 has constant value '83204823 25889395'  [Constant]
- RP2 is highly concentrated with TSC  [High correlation]
- T2C is highly concentrated with API  [High correlation]
- ScanNumber is uniformly distributed  [Uniform]
- ScanNumber has unique values  [Unique]
- LockMassError has unique values  [Unique]
- Pref***** has unique values  [Unique]
- Top95Quantile has unique values  [Unique]
- PeakErrors is an unsupported type, check if it needs cleaning or further analysis  [Unsupported]

FIG. 4B

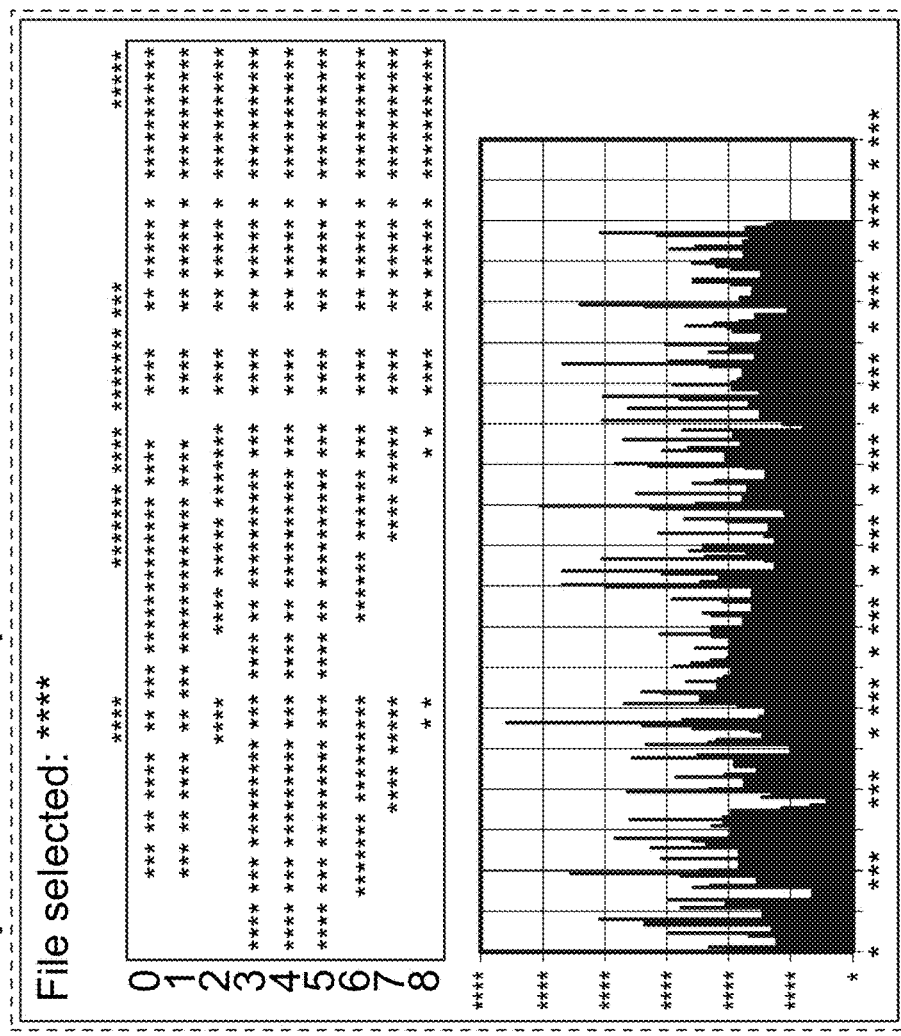
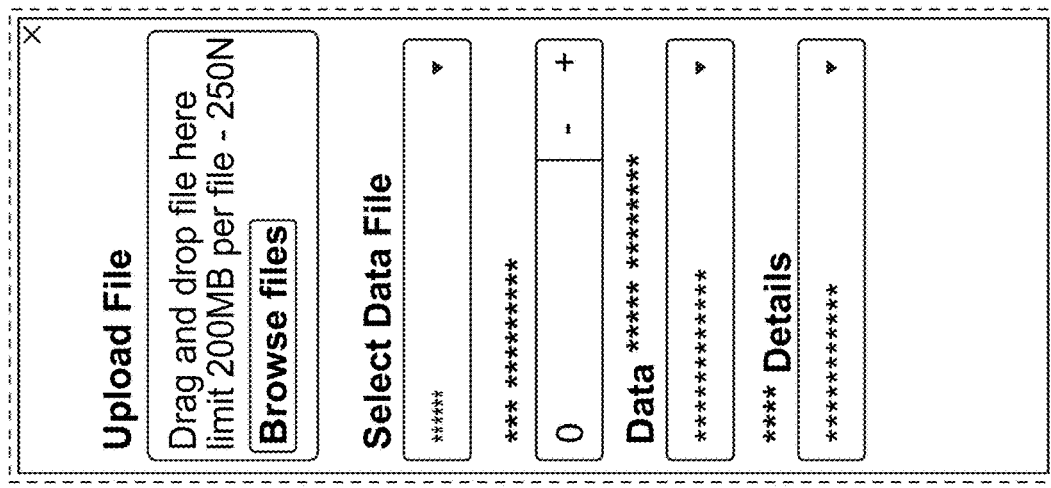
FIG. 4C

METHODS, MEDIUMS, AND SYSTEMS FOR LINKING CHROMATOGRAPHY DATA AND METADATA TO COMPLIANCE RISKS

CROSS-REFERENCE TO RELATED APPLICATIONS

This application claims the benefit of U.S. Provisional Patent Application No. 63/172,953, filed Apr. 9, 2021. The entire disclosure of which is hereby incorporated by reference.

BACKGROUND

Chromatography refers to the separation of a mixture by passing it in solution, suspension, or as a vapor through a medium in which the components of the mixture move at different rates. The components may then be analyzed to identify the existence, amount, concentration, or other properties of the components. Chromatography includes a number of different techniques, such as mass spectrometry (MS), liquid chromatography mass spectrometry (LCMS), and many others.

BRIEF SUMMARY

Exemplary embodiments relate to techniques for analyzing chromatography data and metadata across an enterprise or supply chain in order to identify possible compliance risks. Unless otherwise noted, it is contemplated that these embodiments may be used individually in order to achieve the advantages noted, or in any combination in order to achieve synergistic effects.

As used herein, a compliance risk refers to a circumstance or set of circumstances that do not comply with data integrity best practices, potentially violates regulatory or contractual requirements, are preconfigured situations in which an administrator has required record-keeping for audit purposes, or any other situations in which the process of acquiring or analyzing chromatography data potentially runs afoul of predetermined required conditions. Assessing compliance risks may be important for (e.g.) proactively assessing risks and correcting problematic issues before an audit is conducted by compliance authorities.

Recognizing compliance risks can be a difficult problem when analyzing one's own chromatography data, since it may not be clear when a set of circumstances does or does not constitute a compliance risk. It is even more difficult, however, when working with outside partners or other third parties (e.g., analyzing compliance risks across an enterprise or supply chain) because the third party's data and/or practices may not be made available for analysis. This is particularly common, for instance, in the pharmaceutical industry (where one company may rely on receiving pharmaceutical compounds from outside suppliers). In these situations, it may be necessary to rely on the third party to conduct their own compliance analysis, which may not be the most desirable outcome.

Exemplary embodiments provide visualization and advanced data science on information collected in an analytical data system. Embodiments identify correlations and patterns in chromatography metadata around areas of potential user error. Examples of such metadata include whether some chromatography injections were not processed, whether some injections were processed manually instead of programmatically or in accordance with pre-approved processes, whether some injections were aborted, manually integrated peaks, sign-off records, audit trail records, indicia of performance degradation in the analytical data system (for example, changes to injection data over time), and other information such as a user name of the user conducting the analysis, an instrument ID for the instrument used in the analysis, type of column or solvent used, an instrument location, a server location for a server used to process the data, and what administration privileges were assigned to the users having access to the data. Correlations between these data sources may point to compliance risk areas.

Metadata from the analytical system may be combined with other data sources such as laboratory balances, laboratory access records, and time of data acquisition for the purpose of performing data science for regulatory compliance. The metadata may also be combined with analytical data (e.g., LC data, LCMS data, and other laboratory information sources) to correlate an analytical outcome (such as but not limited to peak shape, concentration of analyte/impurity, retention time) with compliance artifacts. Supervised and/or unsupervised machine learning techniques may be used to combine these data source and learn correlations between them and compliance risks.

The results of these analyses may be displayed on a dashboard or map, allowing a user to visualize compliance risks across an entire enterprise or supply chain. Automatic notifications of compliance risks may be generated and presented on a user interface. A system may also use pattern recognition to provide insights around potential compliance risks that have not yet occurred.

These embodiments will be described in detail below with reference to the accompanying Figures.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 4C illustrates an aspect of the subject matter in accordance with one embodiment.

FIG. 4B illustrates a chromatography compliance data flow in accordance with one embodiment.

DETAILED DESCRIPTION

Figure 1:
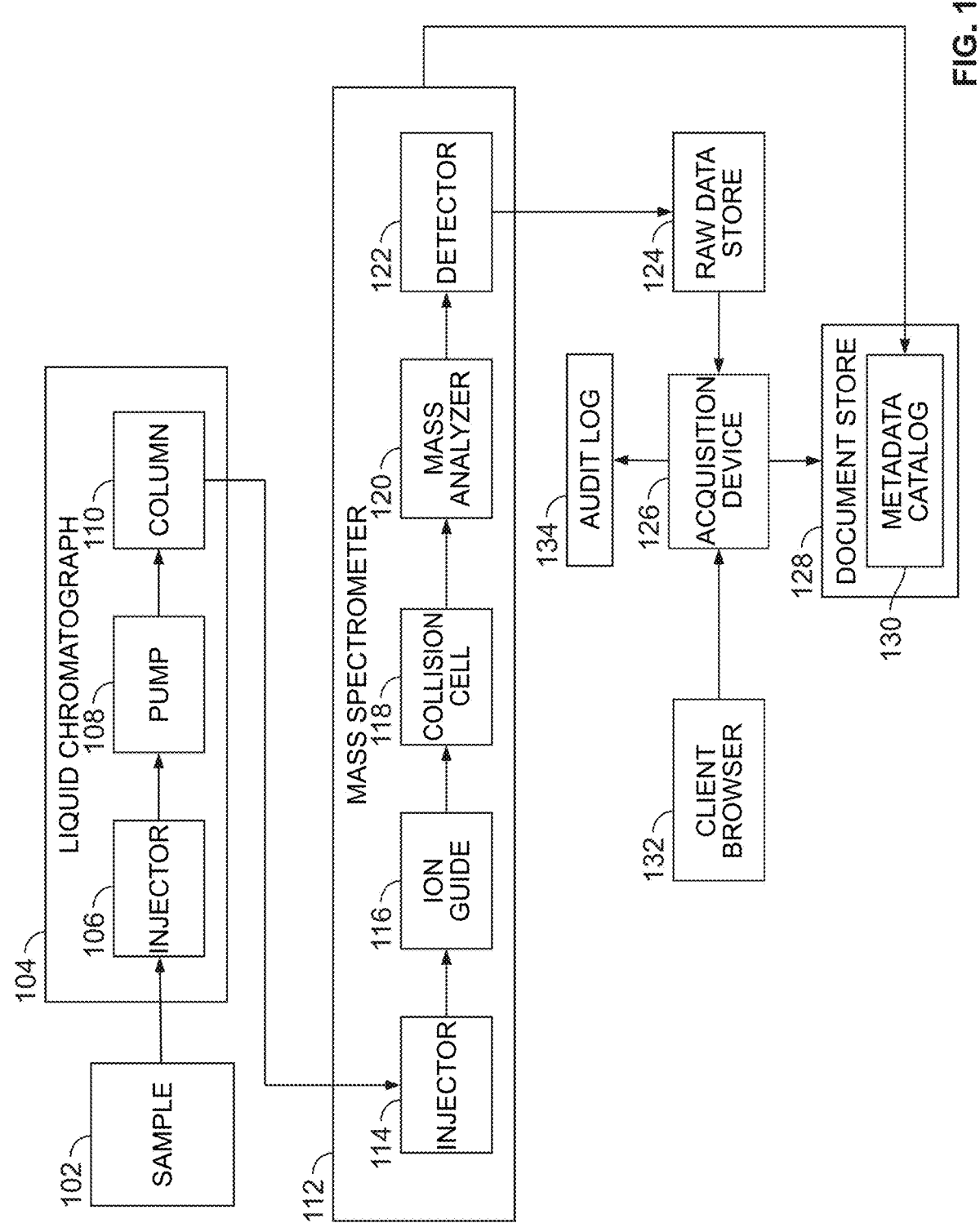
FIG. 1 illustrates an example of a mass spectrometry system according to an exemplary embodiment.

For purposes of illustration, FIG. 1 is a schematic diagram of a system that may be used in connection with techniques herein. Although FIG. 1 depicts particular types of devices in a specific LCMS configuration, one of ordinary skill in the art will understand that different types of chromatographic devices (e.g., LC, MS, tandem MS, etc.) may also be used in connection with the present disclosure. In particular, it is contemplated that exemplary embodiments may be particularly well-suited to use with an LC system, especially when used without an accompanying MS apparatus. Exemplary embodiments may also be used in conjunction with other data sources than the ones depicted and described in detail herein, especially large-scale chromatography (such as the GE Akta system), NMR, IR, CE etc.

A sample 102 is injected into a liquid chromatograph 104 through an injector 106. A pump 108 pumps the sample through a column 110 to separate the mixture into component parts according to retention time through the column.

The output from the column is input to a mass spectrometer 112 for analysis. Initially, the sample is desolved and ionized by a desolvation/ionization device 114. Desolvation can be any technique for desolvation, including, for example, a heater, a gas, a heater in combination with a gas or other desolvation technique. Ionization can be by any ionization techniques, including for example, electrospray ionization (ESI), atmospheric pressure chemical ionization (APCI), matrix assisted laser desorption (MALDI) or other ionization technique. Ions resulting from the ionization are fed to a collision cell 118 by a voltage gradient being applied to an ion guide 116. Collision cell 118 can be used to pass the ions (low-energy) or to fragment the ions (high-energy).

Different techniques (including one described in U.S. Pat. No. 6,717,130, to Bateman et al., which is incorporated by reference herein) may be used in which an alternating voltage can be applied across the collision cell 118 to cause fragmentation. Spectra are collected for the precursors at low-energy (no collisions) and fragments at high-energy (results of collisions).

The output of collision cell 118 is input to a mass analyzer 120. Mass analyzer 120 can be any mass analyzer, including quadrupole, time-of-flight (TOF), ion trap, magnetic sector mass analyzers as well as combinations thereof. A detector 122 detects ions emanating from mass analyzer 122. Detector 122 can be integral with mass analyzer 120. For example, in the case of a TOF mass analyzer, detector 122 can be a microchannel plate detector that counts intensity of ions, i.e., counts numbers of ions impinging it.

A raw data store 124 may provide permanent storage for storing the ion counts for analysis. For example, raw data store 124 can be an internal or external computer data storage device such as a disk, flash-based storage, and the like. An acquisition device 126 analyzes the stored data. Data can also be analyzed in real time without requiring storage in a storage medium 124. In real time analysis, detector 122 passes data to be analyzed directly to computer 126 without first storing it to permanent storage.

Collision cell 118 performs fragmentation of the precursor ions. Fragmentation can be used to determine the primary sequence of a peptide and subsequently lead to the identity of the originating protein. Collision cell 118 includes a gas such as helium, argon, nitrogen, air, or methane. When a charged precursor interacts with gas atoms, the resulting collisions can fragment the precursor by breaking it up into resulting fragment ions.

Metadata describing various parameters related to data acquisition may be generated alongside the raw data. This information may include a configuration of the liquid chromatograph 104 or mass spectrometer 112 (or other chromatography apparatus that acquires the data), which may define a data type, temperatures (e.g., of the laboratory or LC system), and others discussed in more detail below. An identifier (e.g., a key) for a codec that is configured to decode the data may also be stored as part of the metadata and/or with the raw data. The metadata may be stored in a metadata catalog 130 in a document store 128.

The acquisition device 126 may operate according to a workflow, providing visualizations of data to an analyst at each of the workflow steps and allowing the analyst to generate output data by performing processing specific to the workflow step. The workflow may be generated and retrieved via a client browser 132. As the acquisition device 126 performs the steps of the workflow, it may read raw data from a stream of data located in the raw data store 124. As the acquisition device 126 performs the steps of the workflow, it may generate processed data that is stored in a metadata catalog 130 in a document store 128; alternatively or in addition, the processed data may be stored in a different location specified by a user of the acquisition device 126. It may also generate audit records that may be stored in an audit log 134.

Figure 7:
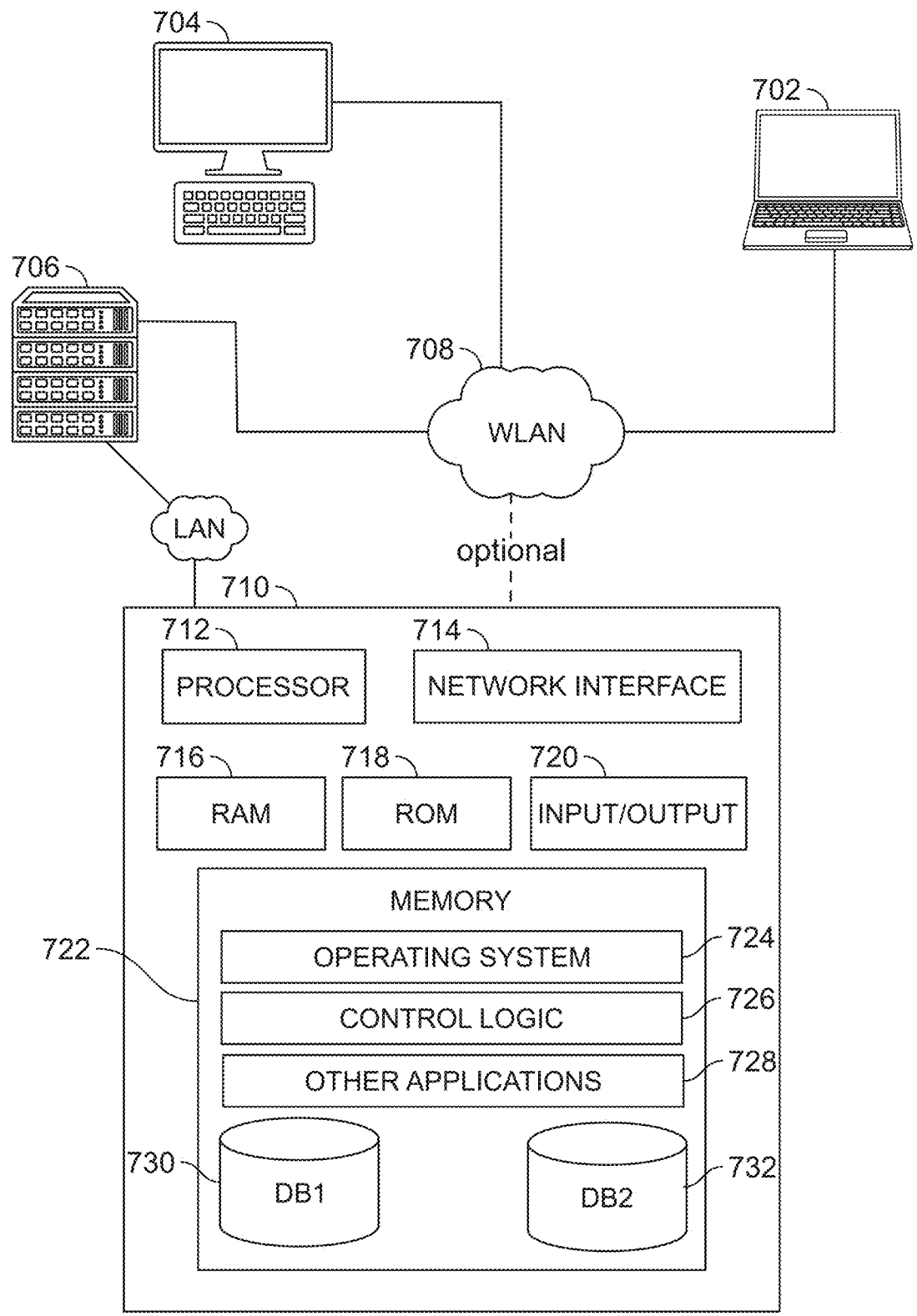
FIG. 7 depicts an illustrative computer system architecture that may be used to practice exemplary embodiments described herein.

The exemplary embodiments described herein may be performed at the client browser 132 and acquisition device 126, among other locations. An example of a device suitable for use as an acquisition device 126 and/or client browser 132, as well as various data storage devices, is depicted in FIG. 7. Servers and other computer hardware can either be on a local network or using cloud technology.

Figure 2:
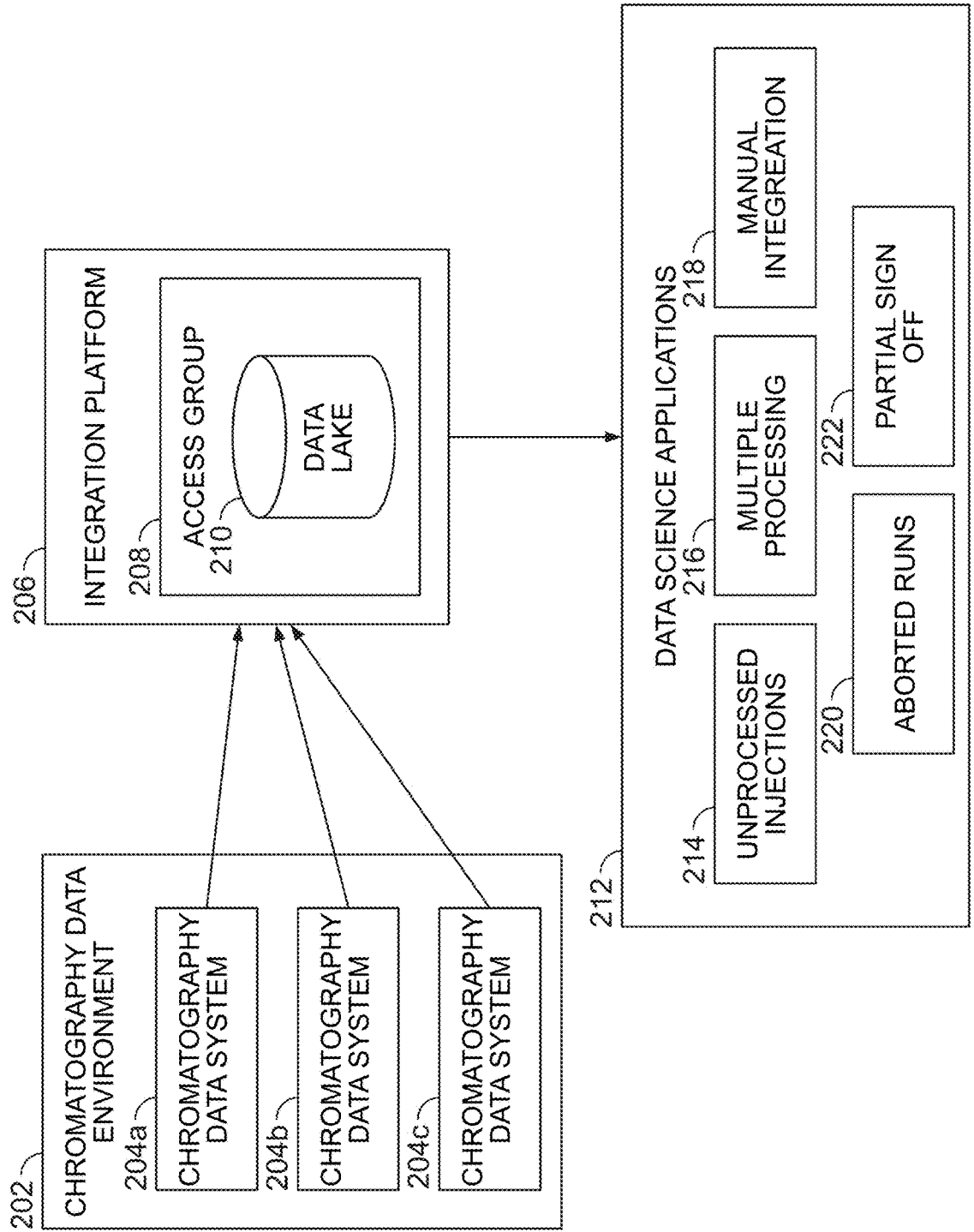
FIG. 2 illustrates an example of a chromatography data environment in accordance with one embodiment.

FIG. 2 depicts an exemplary system suitable for use with exemplary embodiments. The system includes a chromatography data environment 202 configured to manage the acquisition and storage of chromatography data from chromatography data systems 204a, 204b, 204c, . . . . The chromatography data systems 204a, 204b, 204c, . . . may upload their data to an integration platform 206 configured to store data to data lake 210 along with metadata such a timestamp indicating when the data was captured or uploaded to the data lake, identifying characteristics of the components of or of the configuration of the chromatography data system, format characteristics sufficient to identify the format that the data is in, and/or to extract data from the CDSes and standardize the data acquired by different instruments, different types of instruments, in different laboratories, etc. The data may be stored in a data lake 210 in an access group 208. Different parent organizations (e.g., different companies performing chromatography experiments) may each control a different data lake 210, and access to the data in the respective data lake 210 may be managed based on the access group 208.

In some embodiments, third parties may be capable of requesting the right to review data in a given access group 208 from the parent organization that controls the access group 208. This may allow the requesting organization to review the data for potential compliance issues. For example, the reviewing organization may apply one or more data science applications 212 to analyze the data and identify compliance issues. Examples of data science applications 212 include applications configured to consider, in isolation or in combination: whether some injections acquired in the chromatography data environment 202 were not processed (and or a number of unprocessed injections 214); whether some injections were processed multiple times (multiple processing 216); whether some of the data was subjected to manual integration 218; whether some of the chromatography data runs were aborted (aborted runs 220); and whether the data was subjected to partial sign off 222, among other possibilities discussed in more detail below.

Figure 3A:
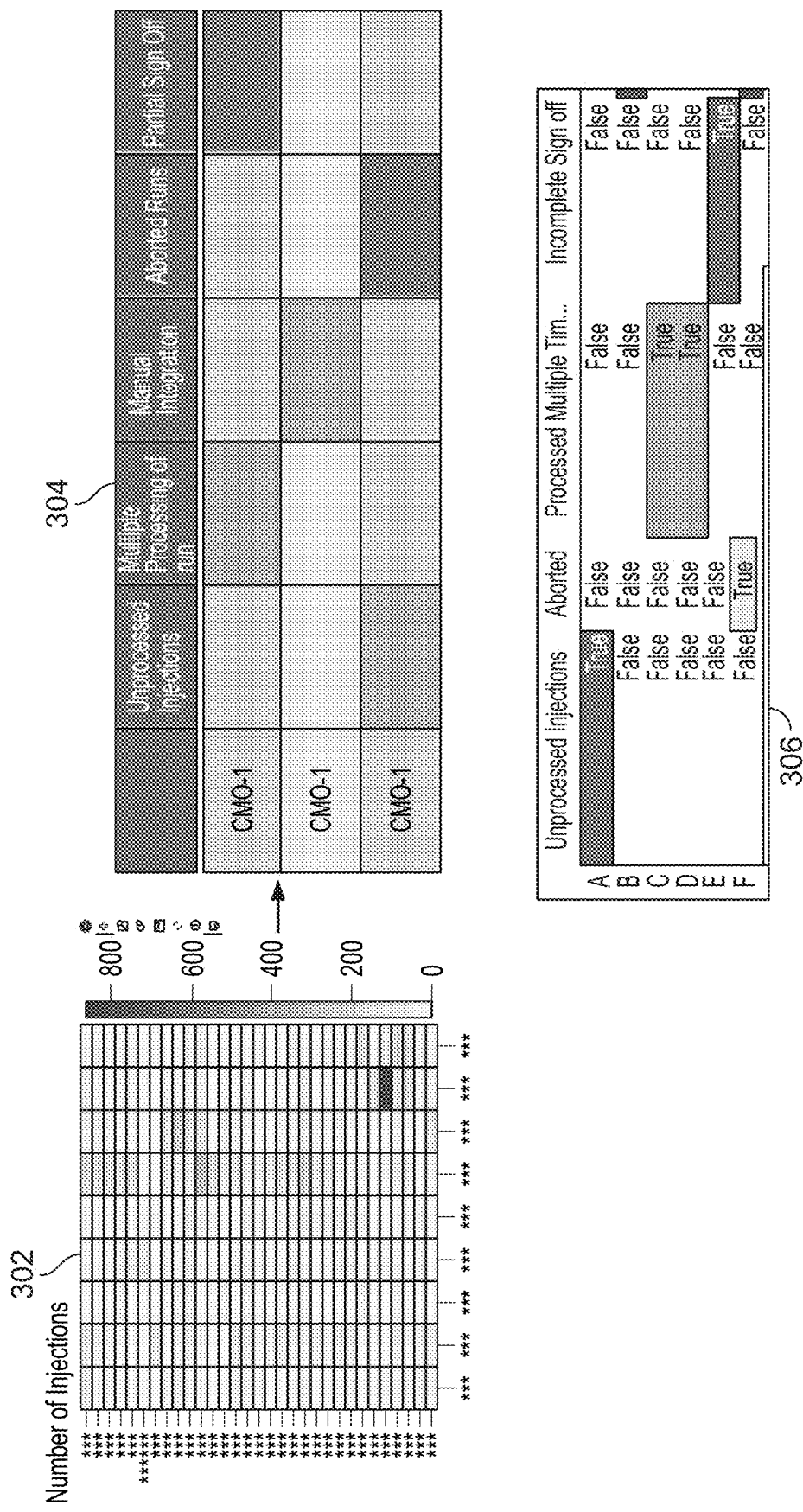
FIG. 3A—FIG. 3C illustrate examples of compliance dashboards in accordance with exemplary embodiments.

When compliance issues are identified by the data science applications 212, the results may be displayed in a dashboard in a compliance graphical user interface. FIG. 3A depicts various compliance plots 302, 304, 306. These plots may be filled in or colored with indicators showing the presence or absence of conditions, such as those noted above, that may be associated (individually or in combination) with a compliance risk. The compliance plots 302, 304, 306 may be displayed on the compliance graphical user interface. Alternatively or in addition, when compliance issues are identified, a notification may be generated and transmitted to a user responsible for monitoring compliance issues. The compliance issues could also trigger an automatic response back into the data system to pause or stop operation of the system. The compliance system can notify personnel or bodies outside of the normal ecosystem to potential risks, such as those risks outlined in a quality management system or regulatory standards.

Figure 3B:
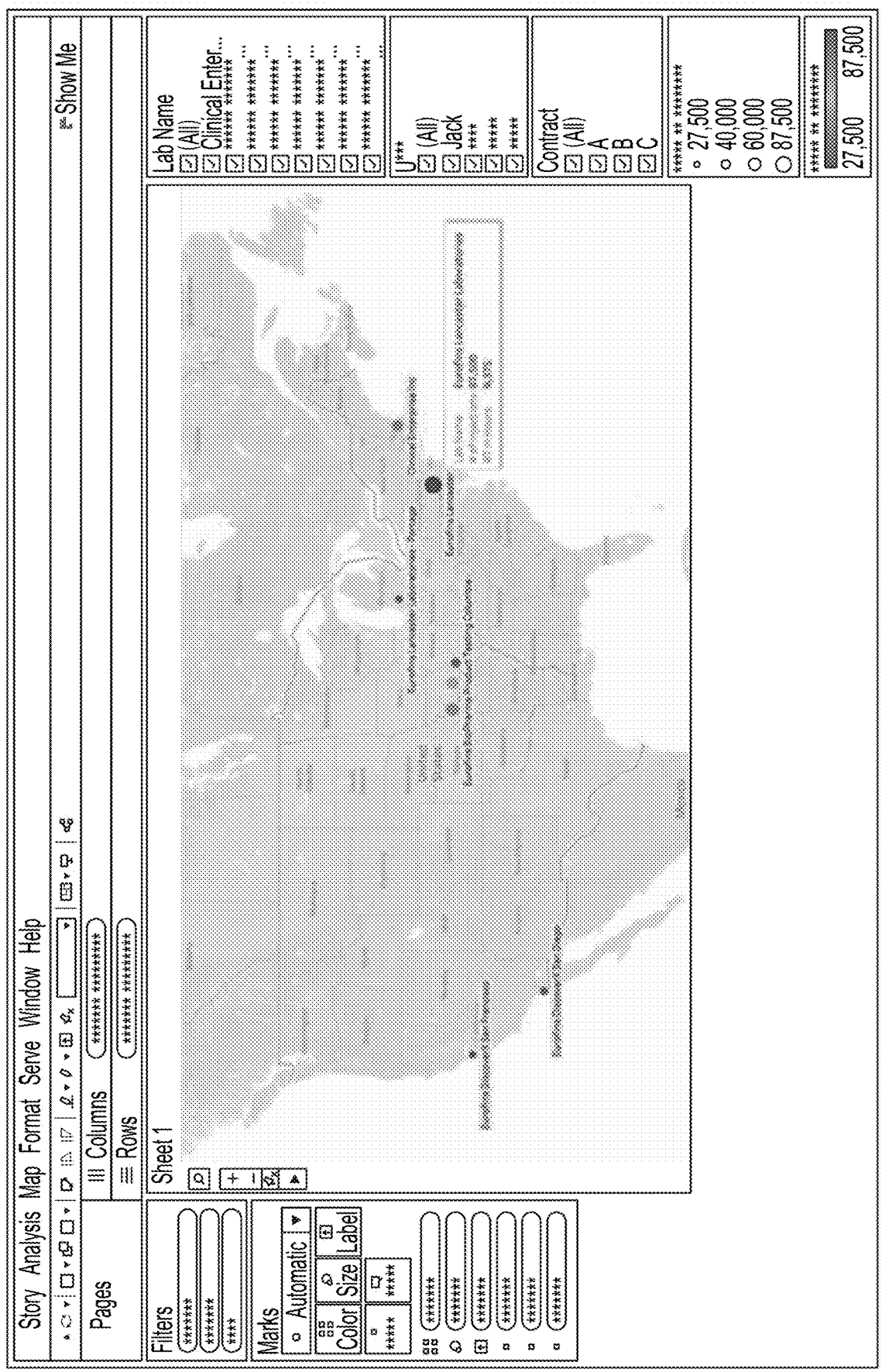
Figure 3C:
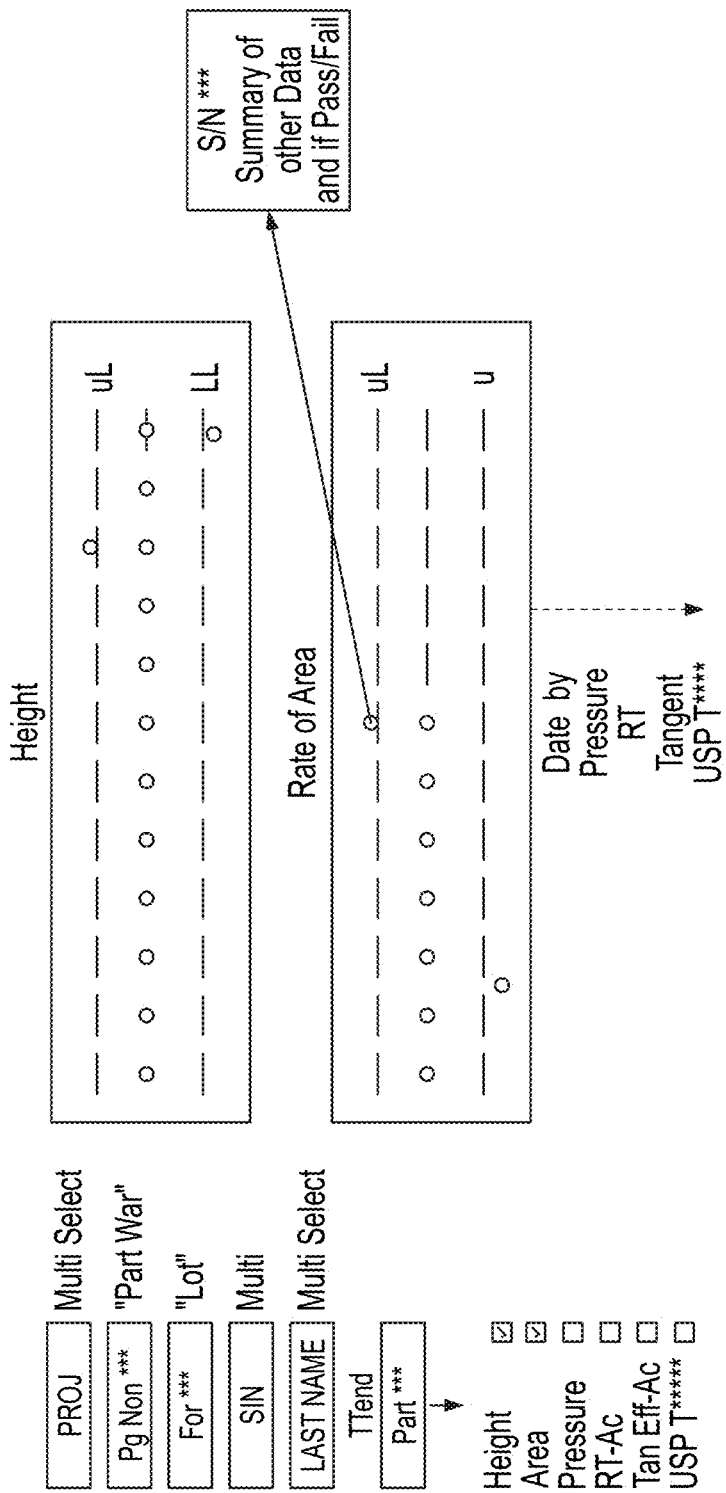

FIG. 3B and FIG. 3C depict alternative implementations of dashboards suitable for use with exemplary embodiments.

A Cascade Architecture for Detecting Faulty Data Acquisition

The compliance issues may be identified using machine learning. Instead of categorical machine learning for predictive analytics, a method is proposed to use "Industry 4.0"/TinyML techniques and a cascade architecture to facilitate the detection of bad data acquisition—faults in chromatography data systems. Using this method greatly simplifies the process of identifying a pool of "exemplar" data that is the basis of modern ML algorithms.

Figure 4A:
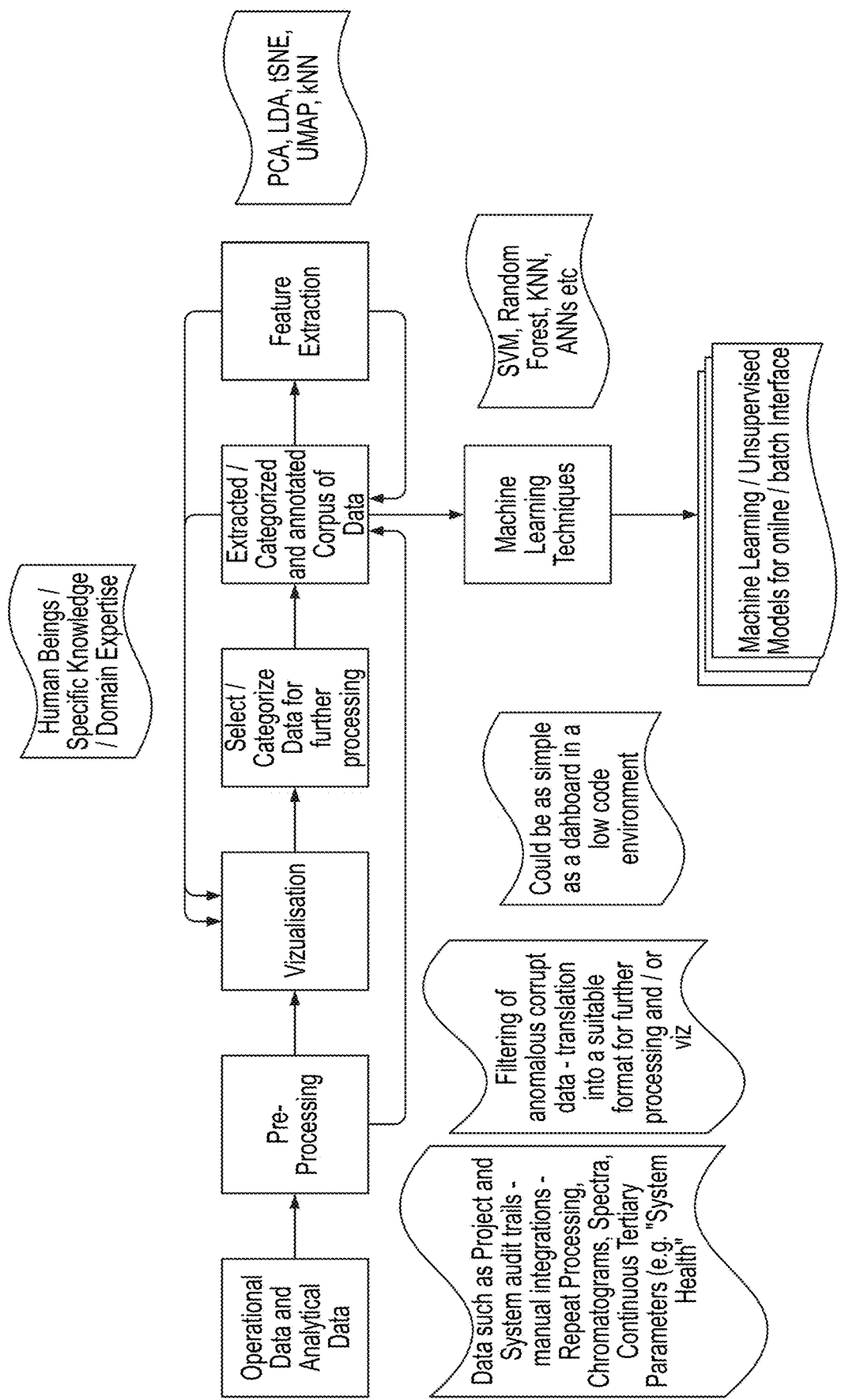
FIG. 4A illustrates an aspect of the subject matter in accordance with one embodiment.

FIG. 4A depicts an exemplary training and visualization pipeline suitable for use with exemplary embodiments. In this pipeline, data processing elements are combined with data visualization elements. Multiple horizontal slices may be made across the pipeline at appropriate locations to separate processing steps into different processes/algorithm combinations.

FIG. 4B and FIG. 4C depict exemplary data explorers for visualizing operational and analytical data. Prior to visualizing the data, it may be pre-processed. This may be as simple as translating from one data format to another (e.g. from Empower data to CSV format for instance). However, at this stage there may be filtering (remove NaN or Null values) or even translation of categorical values to continuous for machine learning or human visualization. In addition at this stage further calculations across multiple continuous values may be performed for instance for MS there may be a calculated FOM (figure of merit) calculated using Resolution and Sensitivity (as well as statistical measures such as skew, kurtosis for instance) and FFT for spectrogram analysis followed by machine vision techniques for supervised learning techniques. At this point there may also be statistical profiling correlation calculations applied (such as provided by a standard library e.g. Pandas that reports correlation information for instance, as in FIG. 4B).

The data may then be visualized in a dashboard such as the one depicted in FIG. 4C. The data explorer of FIG. 4C allows for the visualization of two or more parameters. Using this dashboard, a user may identify outliers or regions of interest, which may be fed into a machine learning algorithm (e.g., kNN clustering). Outliers may be identified using a distance metric, and suitable hyperparameters used by the ML algorithm may include the number of clusters, the distance metric, etc.

Figure 4D:
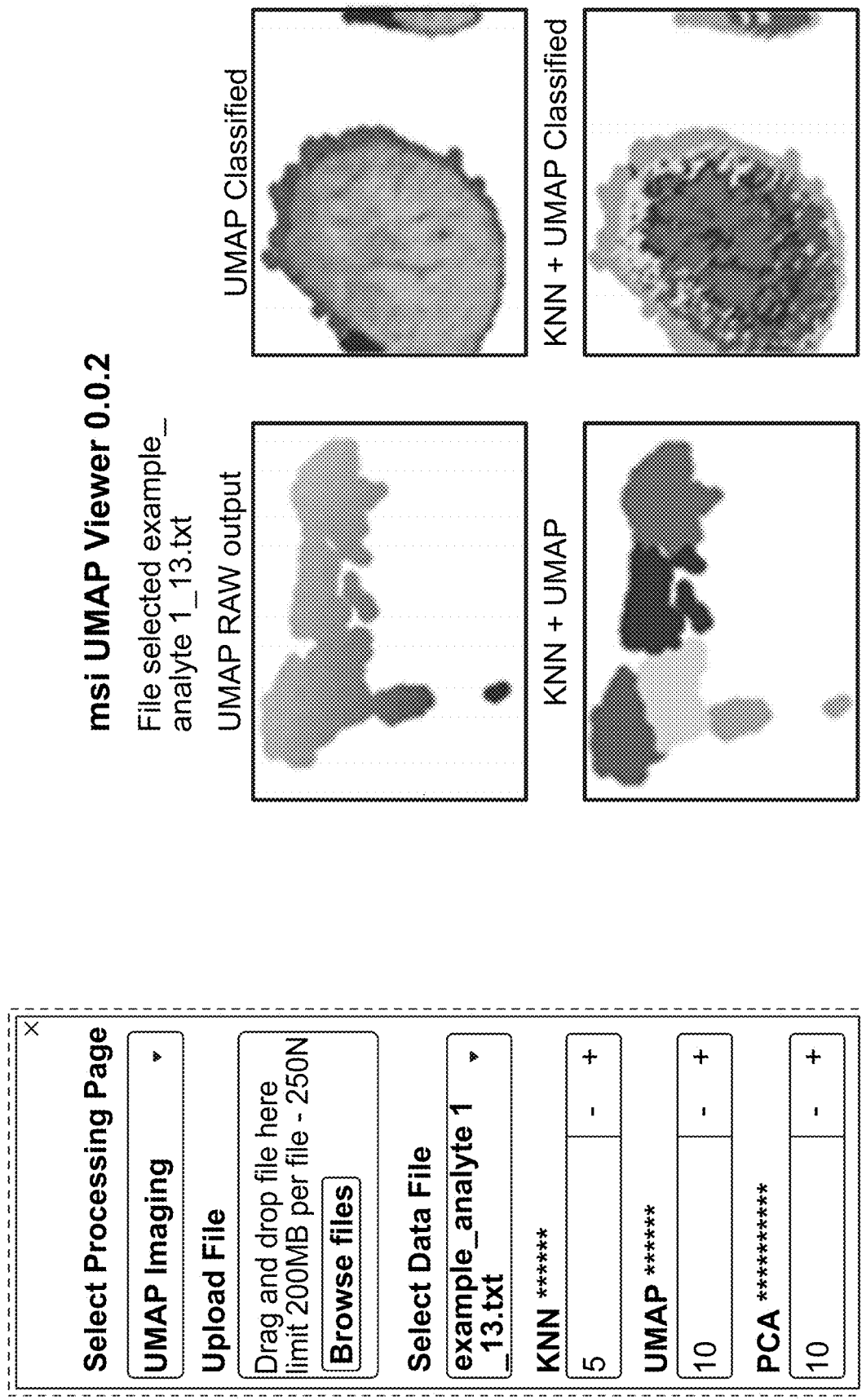
FIG. 4D illustrates an aspect of the subject matter in accordance with one embodiment.

FIG. 4D depicts an example of feature extraction. Feature extraction is the process by which the dimensionality of the data is reduced to something more readily understandable by human beings (or machine). The input data are the dimensions that we wish to reduce on, for instance the number of manual injections, number of times processed, number of sign offs, time between sign offs vs user can be clustered←in this instance the correct number of clusters and distance metrics need to be determined either by user interactions and/or further processing (in this example above the UMAP manifold learning technique coupled to kNN and visualization of the results. Once these parameters are known these can be used online/inline to determine automatically when some data are anomalous or needs to be flagged automatically for further human attention (review by exception/anomaly detection).

Predictions may be made on large batches—that is, run through the whole of the data within a certain (long time frame) and flagged for follow up on any items requiring attention (or simply visualize a trend for example). Trending analysis over time of things like pump pressure, charge current being drawn, time take to process injections or time between injections per user may lead to insights in the data that may be readily identifiable by a human operator or if threshold is used for automatic flagging and communication to a human supervisor. (after collating/histogramming and looking at highest percentile e.g. the 5% longest times taken to process or the 5% shortest).

Predictions may be made in "real time" upon request. Anomalous behavior detection may be performed based on a number of collated input parameter observations on a particular activity. For instance, on a delete action (a trigger), present a group of specified input parameters to the model for a prediction (Flag for follow up or OK status automatically).

Figure 4E:
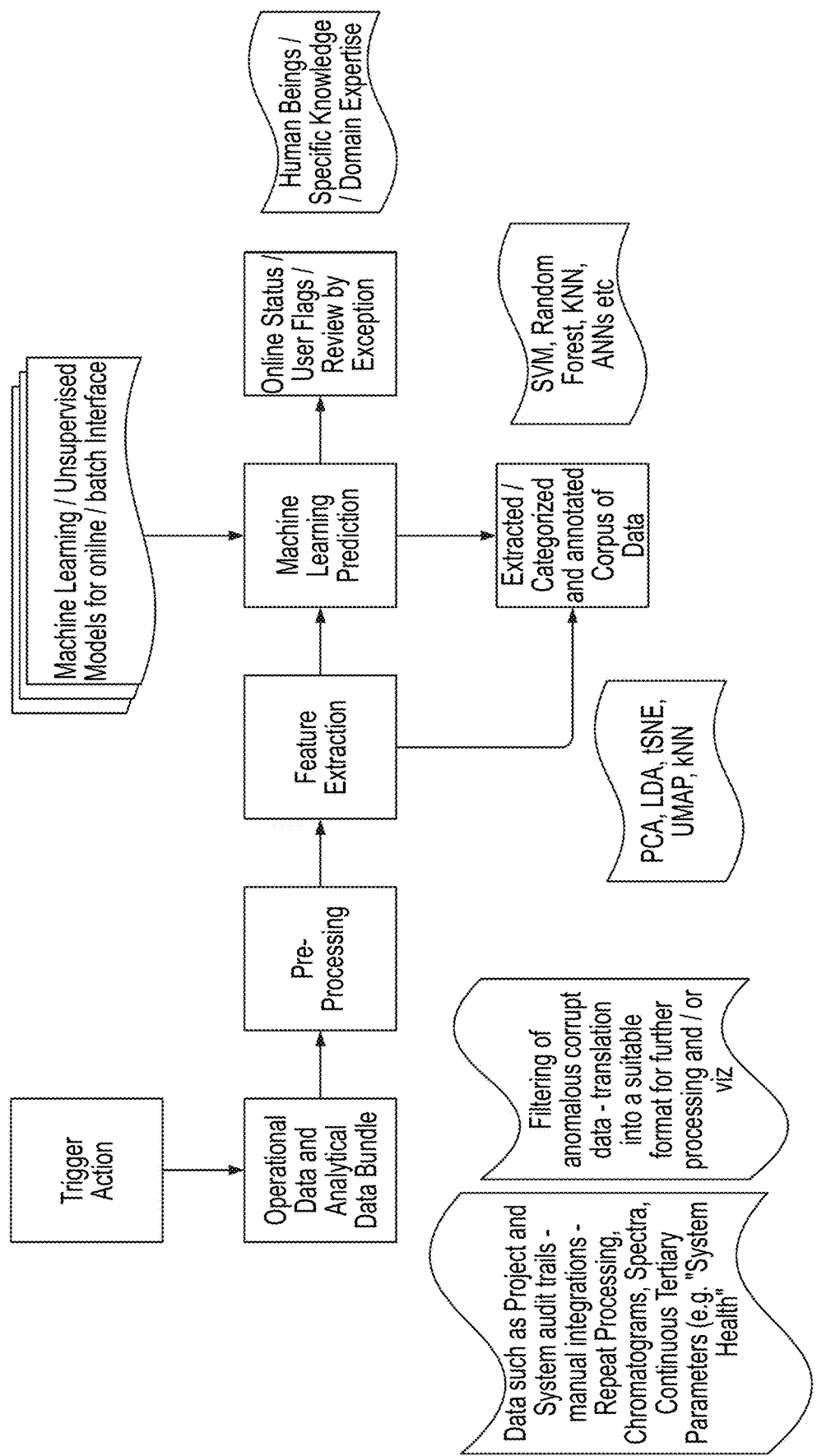
FIG. 4E illustrates an aspect of the subject matter in accordance with one embodiment.

FIG. 4E brings these concepts and data explorers together into a visualization pipeline. The results of the visualization pipeline may be used to train a machine learning algorithm.

Figure 4F:
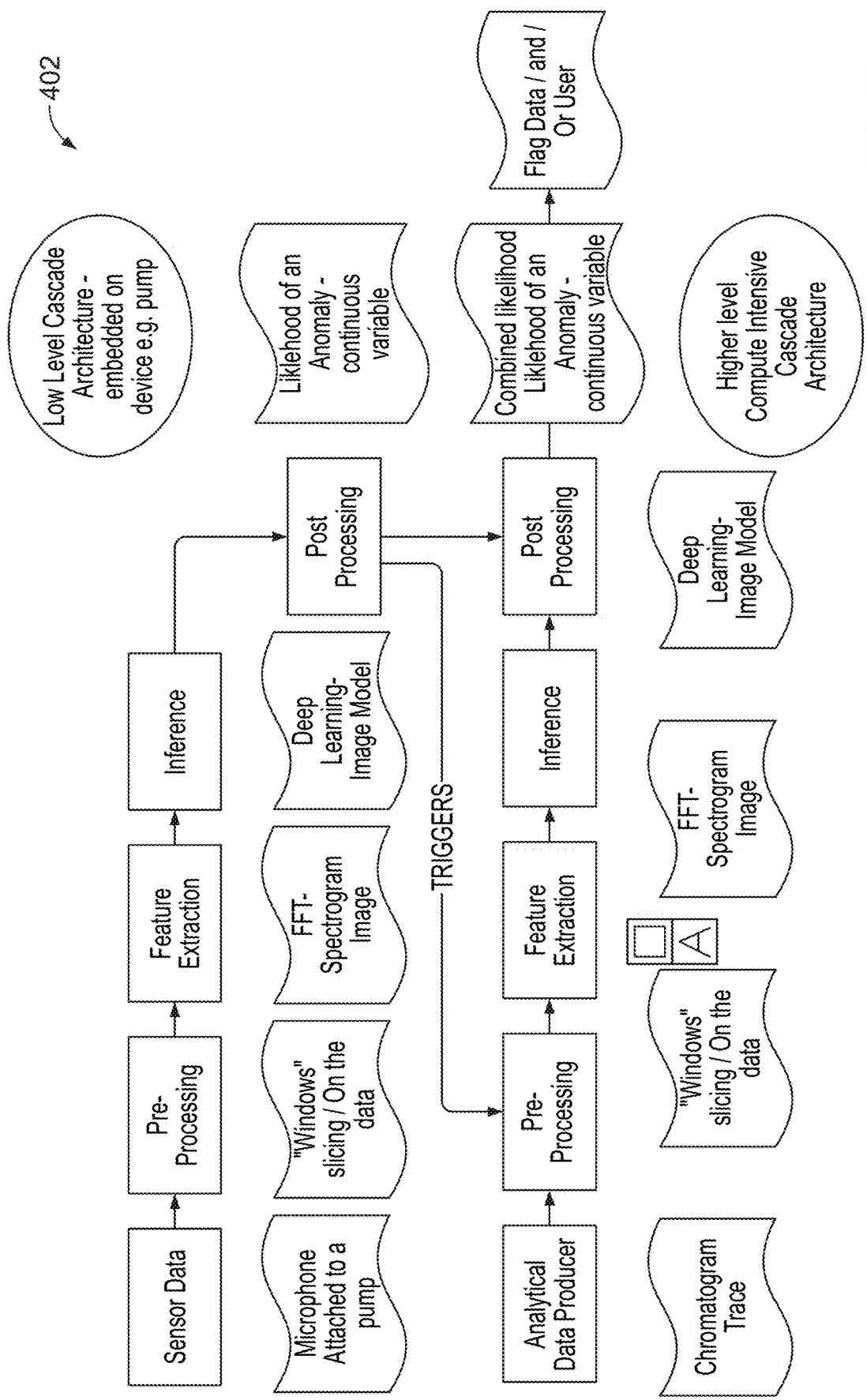
FIG. 4F illustrates an aspect of the subject matter in accordance with one embodiment.

For instance, FIG. 4F depicts a machine learning pipeline suitable for use with exemplary embodiments. Of particular interest are the feature extraction and inference boxes (in this case Fast Fourier Transforms and a Machine Vision DL network) that process continuously streamed data. The data may include both low level sensor data and high-level analytical data coupled in a cascade architecture and combined to give a higher likelihood of anomalous events detection. One of ordinary skill in the art will recognize that FIG. 4F depicts one example of an architecture, although other implementations (e.g., using different types of machine learning or different types of data) are also applicable to the present disclosure.

Exemplary Logic

Figure 5:
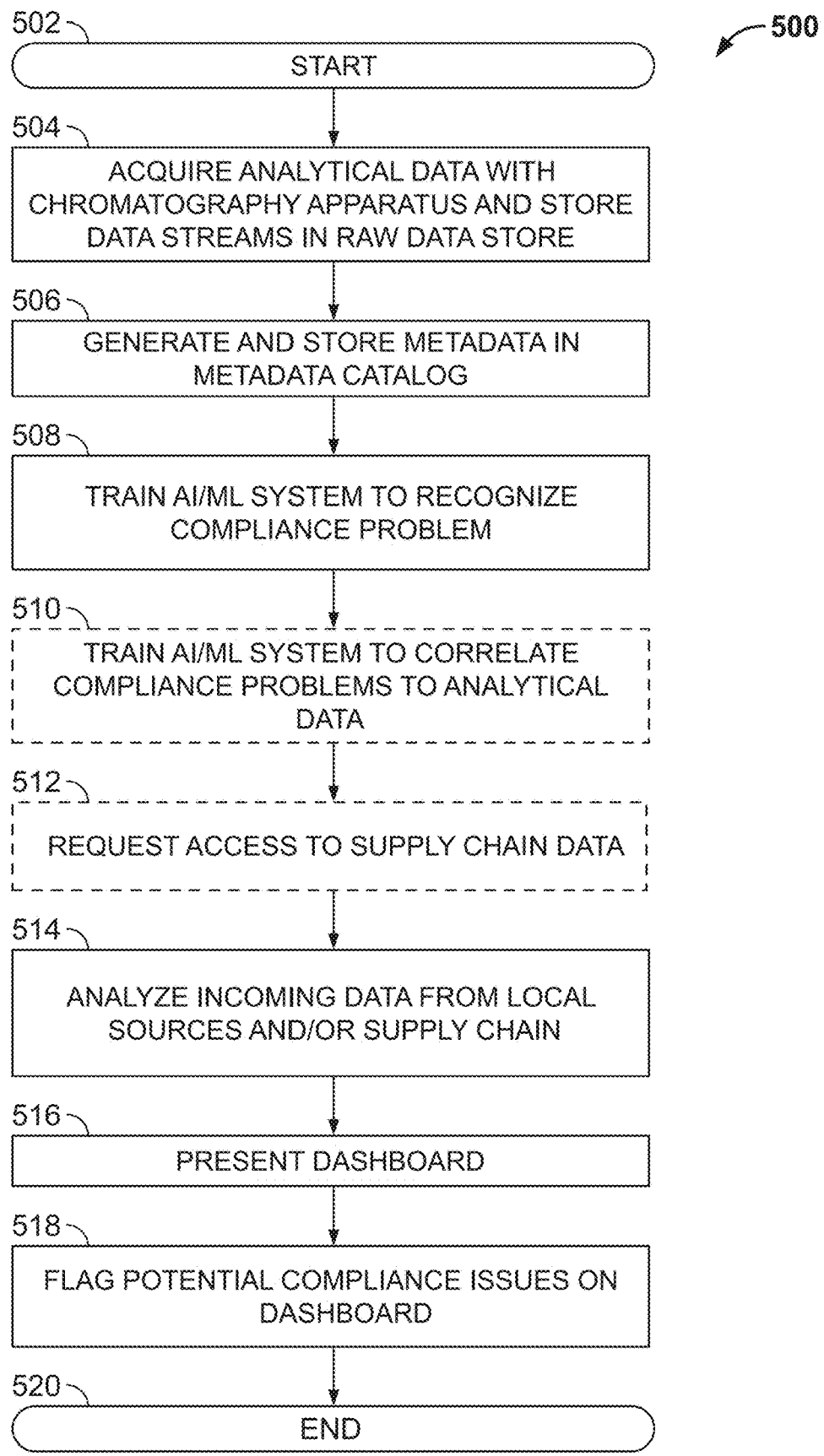
FIG. 5 is a flowchart depicting exemplary logic for analyzing chromatography data in accordance with an exemplary embodiment.

FIG. 5 depicts exemplary compliance analysis logic 500 for storing data in, and retrieving data from, a chromatography data processing environment, and for processing the data to identify potential compliance issues, according to an exemplary embodiment. The compliance analysis logic 500 may be embodied as a computer-implemented method or as instructions stored on a non-transitory computer-readable storage medium and may be configured to cause a processor to perform the logical blocks included in FIG. 5. In some embodiments, the compliance analysis logic 500 may be performed by a computing system configured to perform the logical blocks included in FIG. 5.

Processing starts at start block 502. At block 504, a chromatography apparatus may acquire data. For instance, the chromatography apparatus may perform an experiment and output data in the form of a stream of measurements. The chromatography apparatus may store the measurements in a raw data store. At block 506, the chromatography apparatus may generate metadata related to the experiment and may store the metadata in a metadata catalog distinct from the raw data store.

At block 508, the system may train an AI/ML system to recognize a compliance issue. The AI/ML system may be trained by providing labeled training data, where the training data includes metadata, additional parameters, and/or analytical data, and is labeled with a flag indicating whether the data is associated with a compliance issue. By applying an AI/ML algorithm, a relationship between the data, metadata, and/or additional parameters and potential compliance issues can be learned.

In some embodiments, it may be simpler to identify when a compliance issue exists by examining the metadata and other parameters, as opposed to the analytical data. For example, the metadata may include an indicator of whether the experiment was associated with a manually-processed peak. As opposed to programmatically processing peaks according to known methods, a manually-processed peak may indicate that a user observed the chromatography data and opted to apply custom settings configured to yield a desired result (instead of a more objective result). The resulting analytical data may appear very similar to data generated by a compliant experiment, and so it may be difficult to learn when a compliance issue exists from the analytical data itself. However, when a compliance issue is identified based on the metadata and other parameters, it may then be possible to apply this understanding to label the analytical data and identify features in the analytical data (e.g., peak shape, tailing factors, column degradation profile, etc.) that may be indicative of compliance problems.

To that end, at block 510 the system may optionally train an AI/ML system (the same system as was trained in block 508, or a different system) to correlate compliance problems to the analytical data.

Once trained, the AI/ML system(s) may then be used to analyze new chromatography data to determine whether compliance issues may exist in the new chromatography data. The new chromatography data may originate with the user/organization applying the compliance analysis, or with a third party (such as suppliers of the analyzing organization in a supply chain). To that end, it may be necessary for the current user/organization to request access rights to the third-party data in a data lake at block 512. The third-party may provide limited access rights allowing the data to be analyzed for compliance purposes.

At block 514, the local and/or third-party data may be analyzed using the trained AI/ML system(s) for compliance issues. Compliance issues may be identified based on one or more rules, such as a parameter value being toggled to true or exceeding a predefined threshold value. In some embodiments, compliance issues may be identified based on trends in the data (e.g., determining that a compliance issue does not exist, but if the data continues on its current trend, a compliance issue will exist within a predetermined time limit).

Any problematic conditions may be displayed, at block 516 and block 518, in a compliance dashboard on a compliance user interface (see, e.g., FIG. 3A). If the system determines that a compliance issue is likely (e.g., the AI/ML system determines that a probability of a compliance issue is more than a predetermined threshold value), then the system may generate a notification or alert and transmit the notification/alert to a user responsible for monitoring compliance.

Processing may then proceed to done block 520 and terminate.

Figure 6:
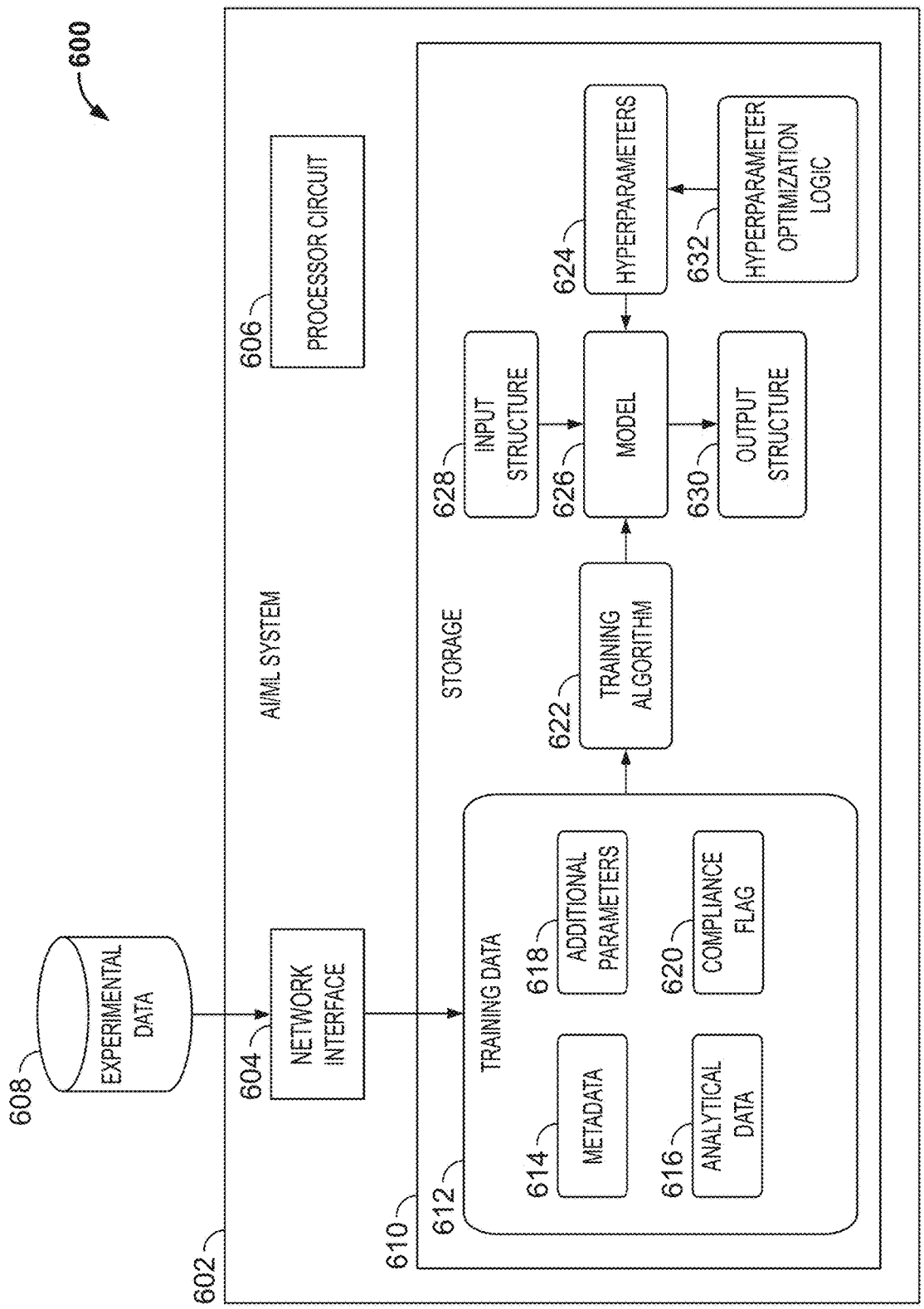
FIG. 6 illustrates an exemplary artificial intelligence/machine learning (AI/ML) system suitable for use with exemplary embodiments.

In order to learn associations between metadata and compliance issues (and/or between compliance issues and analytical data), artificial intelligence/machine learning (AI/ML) may be applied. To that end, FIG. 6 depicts an AI/ML environment 600 suitable for use with exemplary embodiments.

The AI/ML environment 600 may include an AI/ML System 602, such as a computing device that applies an AI/ML algorithm to learn relationships between the above-noted protein parameters.

The AI/ML System 602 may make use of experimental data 608 returned by an experimental apparatus 118 as (or after) chromatography data is collected. In some cases, the experimental data 608 may include pre-existing experimental data from databases, libraries, repositories, etc. The experimental data 608 may be collocated with the AI/ML System 602 (e.g., stored in a Storage 610 of the AI/ML System 602), may be remote from the AI/ML System 602 and accessed via a Network Interface 604, or may be a combination of local and remote data.

In the Training Data 612, the experimental data returned from experimental apparatuses may be supplemented by data learned by modeling and simulating chromatography data collection in software, and by parsing scientific and academic literature for information about the relationships.

As noted above, the AI/ML System 602 may include a Storage 610, which may include a hard drive, solid state storage, and/or random-access memory. The storage may hold Training Data 612, which may compare different data and metadata against a classification of whether a compliance issue exists. In one example, these Training Data 612 may include the metadata 614, Analytical data 616 and/or other additional parameters 618, although other properties may be measured depending on the application. The metadata 614 may include, among other information:

Unprocessed Injections (as an injection that was not processed is generally an indicator that the analyst decided to monitor the run and may not have processed due to poor chromatography),
Manually Processes Injections,
Aborted Injections, and
Manually Integrated Peaks.

The additional parameters 618 may include, among other information:

Sign Off Records,
Audit Trail Records,
User Name,
Instrument ID,
Instrument Location,
Server Location, and
Administration Privileges.

The analytical data 616 may include unprocessed data from a chromatography apparatus and/or processed data.

Some embodiments may be used in conjunction with a machine learning model, such as a neural network, decision tree, support vector machine, etc. In such embodiments, the Training Data 612 may be applied to train a model 626. Depending on the particular application, different types of models 524 may be suitable for use. For instance, in the depicted example, an artificial neural network (ANN) may be particularly well-suited to learning associations between metadata, analytical data, and compliance issues. Similarity and metric distance learning may also be well-suited to this particular type of task, although one of ordinary skill in the art will recognize that different types of models 524 may be used, depending on the designers goals, the resources available, the amount of input data available, etc. Other embodiments may use a model-less AI paradigm, in which case no model 626 is used.

Any suitable Training Algorithm 622 may be used to train the model 626. Nonetheless, the example depicted in FIG. 6 may be particularly well-suited to a supervised training algorithm or reinforcement learning. For a supervised training algorithm, the AI/ML System 602 may apply the Metadata 614 and Additional parameters 618 as input data, to which a compliance flag 620 (indicating whether the data is associated with a compliance issue) may be mapped to learn associations between the inputs and compliance issues.

The Training Algorithm 622 may be applied using a Processor Circuit 606, which may include suitable hardware processing resources that operate on the logic and structures in the Storage 610. The Training Algorithm 622 and/or the development of the trained model 626 may be at least partially dependent on model Hyperparameters 624; in exemplary embodiments, the model Hyperparameters 624 may be automatically selected based on Hyperparameter Optimization logic 632, which may include any known hyperparameter optimization techniques as appropriate to the model 626 selected and the Training Algorithm 622 to be used.

Optionally, the model 626 may be re-trained over time, in order to accommodate new knowledge about proteins and new experiments performed.

In some embodiments, some of the Training Data 612 may be used to initially train the model 626, and some may be held back as a validation subset. The portion of the Training Data 612 not including the validation subset may be used to train the model 626, whereas the validation subset may be held back and used to test the trained model 626 to verify that the model 626 is able to generalize its predictions to new data.

As discussed above, the metadata 614 and additional parameters 618 may be used to learn when a compliance issue exists. Subsequently, the trained model 626 may be applied to the analytical data 616 to learn configurations in the analytical data 616 that signify that a compliance issues may exist. Accordingly, a second model 626 may optionally be trained.

Once the model 626 is trained, it may be applied (by the Processor Circuit 606) to new input data. The new input data may include current metadata 614 and additional parameters 618, and/or may include analytical data 616. This input to the model 626 may be formatted according to a predefined input structure 628 mirroring the way that the Training Data 612 was provided to the model 626. The model 626 may generate an output structure 630 which may be, for example, a prediction of whether a compliance issue exists, given the input data.

The above description pertains to a particular kind of AI/ML System 602, which applies supervised learning techniques given available training data with input/result pairs. However, the present invention is not limited to use with a specific AI/ML paradigm, and other types of AI/ML techniques may be used. For example, in some embodiments the AI/ML System 602 may apply reinforcement learning, in which the AI/ML System 602 may learn a policy or set of rules defining which changes to analytical data 616, metadata 614, and/or additional parameters 618 affect compliance. Other AI/ML techniques, such as evolutionary algorithms, are also contemplated for use with exemplary embodiments.

FIG. 7 illustrates one example of a system architecture and data processing device that may be used to implement one or more illustrative aspects described herein in a standalone and/or networked environment. Various network nodes, such as the data server 710, web server 706, computer 704, and laptop 702 may be interconnected via a wide area network 708 (WAN), such as the internet. Other networks may also or alternatively be used, including private intranets, corporate networks, LANs, metropolitan area networks (MANs) wireless networks, personal networks (PANs), and the like. Network 708 is for illustration purposes and may be replaced with fewer or additional computer networks. A local area network (LAN) may have one or more of any known LAN topology and may use one or more of a variety of different protocols, such as ethernet. Devices data server 710, web server 706, computer 704, laptop 702 and other devices (not shown) may be connected to one or more of the networks via twisted pair wires, coaxial cable, fiber optics, radio waves or other communication media.

Computer software, hardware, and networks may be utilized in a variety of different system environments, including standalone, networked, remote-access (aka, remote desktop), virtualized, and/or cloud-based environments, among others.

The term "network" as used herein and depicted in the drawings refers not only to systems in which remote storage devices are coupled together via one or more communication paths, but also to stand-alone devices that may be coupled, from time to time, to such systems that have storage capability. Consequently, the term "network" includes not only a "physical network" but also a "content network," which is comprised of the data—attributable to a single entity—which resides across all physical networks.

The components may include data server 710, web server 706, and client computer 704, laptop 702. Data server 710 provides overall access, control and administration of databases and control software for performing one or more illustrative aspects described herein. Data server 710 may be connected to web server 706 through which users interact with and obtain data as requested. Alternatively, data server 710 may act as a web server itself and be directly connected to the internet. Data server 710 may be connected to web server 706 through the network 708 (e.g., the internet), via direct or indirect connection, or via some other network. Users may interact with the data server 710 using remote computer 704, laptop 702, e.g., using a web browser to connect to the data server 710 via one or more externally exposed web sites hosted by web server 706. Client computer 704, laptop 702 may be used in concert with data server 710 to access data stored therein or may be used for other purposes. For example, from client computer 704, a user may access web server 706 using an internet browser, as is known in the art, or by executing a software application that communicates with web server 706 and/or data server 710 over a computer network (such as the internet).

Servers and applications may be combined on the same physical machines, and retain separate virtual or logical addresses, or may reside on separate physical machines. FIG. 7 illustrates just one example of a network architecture that may be used, and those of skill in the art will appreciate that the specific network architecture and data processing devices used may vary, and are secondary to the functionality that they provide, as further described herein. For example, services provided by web server 706 and data server 710 may be combined on a single server.

Each component data server 710, web server 706, computer 704, laptop 702 may be any type of known computer, server, or data processing device. Data server 710, e.g., may include a processor 712 controlling overall operation of the data server 710. Data server 710 may further include RAM 716, ROM 718, network interface 714, input/output interfaces 720 (e.g., keyboard, mouse, display, printer, etc.), and memory 722. Input/output interfaces 720 may include a variety of interface units and drives for reading, writing, displaying, and/or printing data or files. Memory 722 may further store operating system software 724 for controlling overall operation of the data server 710, control logic 726 for instructing data server 710 to perform aspects described herein, and other application software 728 providing secondary, support, and/or other functionality which may or may not be used in conjunction with aspects described herein. The control logic may also be referred to herein as the data server software control logic 726. Functionality of the data server software may refer to operations or decisions made automatically based on rules coded into the control logic, made manually by a user providing input into the system, and/or a combination of automatic processing based on user input (e.g., queries, data updates, etc.).

Memory 1122 may also store data used in performance of one or more aspects described herein, including a first database 732 and a second database 730. In some embodiments, the first database may include the second database (e.g., as a separate table, report, etc.). That is, the information can be stored in a single database, or separated into different logical, virtual, or physical databases, depending on system design. Web server 706, computer 704, laptop 702 may have similar or different architecture as described with respect to data server 710. Those of skill in the art will appreciate that the functionality of data server 710 (or web server 706, computer 704, laptop 702) as described herein may be spread across multiple data processing devices, for example, to distribute processing load across multiple computers, to segregate transactions based on geographic location, user access level, quality of service (QoS), etc.

One or more aspects may be embodied in computer-usable or readable data and/or computer-executable instructions, such as in one or more program modules, executed by one or more computers or other devices as described herein. Generally, program modules include routines, programs, objects, components, data structures, etc. that perform particular tasks or implement particular abstract data types when executed by a processor in a computer or other device. The modules may be written in a source code programming language that is subsequently compiled for execution or may be written in a scripting language such as (but not limited to) HTML or XML. The computer executable instructions may be stored on a computer readable medium such as a nonvolatile storage device. Any suitable computer readable storage media may be utilized, including hard disks, CD-ROMs, optical storage devices, magnetic storage devices, and/or any combination thereof. In addition, various transmission (non-storage) media representing data or events as described herein may be transferred between a source and a destination in the form of electromagnetic waves traveling through signal-conducting media such as metal wires, optical fibers, and/or wireless transmission media (e.g., air and/or space). various aspects described herein may be embodied as a method, a data processing system, or a computer program product. Therefore, various functionalities may be embodied in whole or in part in software, firmware and/or hardware or hardware equivalents such as integrated circuits, field programmable gate arrays (FPGA), and the like. Particular data structures may be used to more effectively implement one or more aspects described herein, and such data structures are contemplated within the scope of computer executable instructions and computer-usable data described herein.

The components and features of the devices described above may be implemented using any combination of discrete circuitry, application specific integrated circuits (ASICs), logic gates and/or single chip architectures. Further, the features of the devices may be implemented using microcontrollers, programmable logic arrays and/or microprocessors or any combination of the foregoing where suitably appropriate. It is noted that hardware, firmware and/or software elements may be collectively or individually referred to herein as "logic" or "circuit."

It will be appreciated that the exemplary devices shown in the block diagrams described above may represent one functionally descriptive example of many potential implementations. Accordingly, division, omission or inclusion of block functions depicted in the accompanying figures does not infer that the hardware components, circuits, software and/or elements for implementing these functions would be necessarily be divided, omitted, or included in embodiments.

At least one computer-readable storage medium may include instructions that, when executed, cause a system to perform any of the computer-implemented methods described herein.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Moreover, unless otherwise noted the features described above are recognized to be usable together in any combination. Thus, any features discussed separately may be employed in combination with each other unless it is noted that the features are incompatible with each other.

With general reference to notations and nomenclature used herein, the detailed descriptions herein may be presented in terms of program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic, or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein, which form part of one or more embodiments. Rather, the operations are machine operations. Useful machines for performing operations of various embodiments include general purpose digital computers or similar devices.

Some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Various embodiments also relate to apparatus or systems for performing these operations. This apparatus may be specially constructed for the required purpose or it may comprise a general-purpose computer as selectively activated or reconfigured by a computer program stored in the computer. The procedures presented herein are not inherently related to a particular computer or other apparatus. Various general-purpose machines may be used with programs written in accordance with the teachings herein, or it may prove convenient to construct more specialized apparatus to perform the required method steps. The required structure for a variety of these machines will appear from the description given.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims.

What is claimed is:

1. A computer-implemented method comprising:
    requesting input information relating to a chromatography experiment from a data lake, the input information comprising metadata relating to how the chromatography experiment was performed, wherein the metadata comprises at least one of: whether the chromatography experiment included an unprocessed injection; whether the chromatography experiment included a manually processed injection, whether the chromatography experiment included an aborted injection; or whether the chromatography experiment was associated with a manually integrated peak;
    applying machine learning to identify a relationship between the metadata and whether a compliance issue exists with regards to the chromatography experiment;
    applying the identified relationship to new chromatography input information, the new chromatography input information including a new configuration of metadata; and
    flagging one or more parameters in the new configuration of metadata contributing to a compliance issue in a dashboard user interface.

2. The computer-implemented method of claim 1, wherein the input information further includes one or more additional parameters used in the machine learning, the one or more additional parameters comprising at least one of: a sign off record; an audit trail record; a user name; an instrument identifier; an instrument location; a server location; or administrative privileges assigned in the chromatography experiment.

3. The computer-implemented method of claim 1, wherein the input information further includes analytical data from the chromatography experiment, further comprising applying machine learning to learn a relationship between the analytical data and whether a compliance issue exists with regards to the chromatography experiment, wherein the relationship is based on one or more of a peak shape, tailing factors, or a column degradation profile.

4. The computer-implemented method of claim 1, wherein the new chromatography input information is third-party chromatography experiment information, and further comprising requesting access to the third-party chromatography experiment information from an access group.

5. The computer-implemented method of claim 4, wherein the third-party chromatography experiment information is derived from chromatography experiments associated with a supply chain not under the direct supervision of an entity requesting a compliance analysis.

6. The computer-implemented method of claim 1, further comprising applying pattern recognition to the new chromatography input information to predict a likelihood of a compliance issue that has not yet occurred.

7. A non-transitory computer-readable storage medium, the computer-readable storage medium including instructions that when executed by a computer, cause the computer to:
    request input information relating to a chromatography experiment from a data lake, the input information comprising metadata relating to how the chromatography experiment was performed, wherein the metadata comprises at least one of: whether the chromatography experiment included an unprocessed injection; whether the chromatography experiment included a manually processed injection, whether the chromatography experiment included an aborted injection; or whether the chromatography experiment was associated with a manually integrated peak;
    apply machine learning to identify a relationship between the metadata and whether a compliance issue exists with regards to the chromatography experiment;
    apply the identified relationship to new chromatography input information, the new chromatography input information including a new configuration of metadata; and flag one or more parameters in the new configuration of metadata contributing to a compliance issue in a dashboard user interface.

8. The computer-readable storage medium of claim 7, wherein the input information further includes one or more additional parameters used in the machine learn, the one or more additional parameters comprising at least one of: a sign off record; an audit trail record; a user name; an instrument identifier; an instrument location; a server location; or administrative privileges assigned in the chromatography experiment.

9. The computer-readable storage medium of claim 7, wherein the input information further includes analytical data from the chromatography experiment, wherein the instructions further configure the computer to apply machine learning to learn a relationship between the analytical data and whether a compliance issue exists with regards to the chromatography experiment, wherein the relationship is based on one or more of a peak shape, tailing factors, or a column degradation profile.

10. The computer-readable storage medium of claim 7, wherein the new chromatography input information is third-party chromatography experiment information, and wherein the instructions further configure the computer to request access to the third-party chromatography experiment information from an access group.

11. The computer-readable storage medium of claim 10, wherein the third-party chromatography experiment information is derived from chromatography experiments associated with a supply chain not under the direct supervision of an entity request a compliance analysis.

12. The computer-readable storage medium of claim 7, wherein the instructions further configure the computer to apply pattern recognition to the new chromatography input information to predict a likelihood of a compliance issue that has not yet occurred.

13. A computing apparatus comprising:
a processor; and
a memory storing instructions that, when executed by the processor, configure the apparatus to:
request input information relating to a chromatography experiment from a data lake, the input information comprising metadata relating to how the chromatography experiment was performed, wherein the metadata comprises at least one of: whether the chromatography experiment included an unprocessed injection; whether the chromatography experiment included a manually processed injection, whether the chromatography experiment included an aborted injection; or whether the chromatography experiment was associated with a manually integrated peak;
apply machine learning to identify a relationship between the metadata and whether a compliance issue exists with regards to the chromatography experiment;
apply the identified relationship to new chromatography input information, the new chromatography input information including a new configuration of metadata; and
flag one or more parameters in the new configuration of metadata contributing to a compliance issue in a dashboard user interface.

14. The computing apparatus of claim 13, wherein the input information further includes one or more additional parameters used in the machine learn, the one or more additional parameters comprising at least one of: a sign off record; an audit trail record; a user name; an instrument identifier; an instrument location; a server location; or administrative privileges assigned in the chromatography experiment.

15. The computing apparatus of claim 13, wherein the input information further includes analytical data from the chromatography experiment, wherein the instructions further configure the apparatus to apply machine learning to learn a relationship between the analytical data and whether a compliance issue exists with regards to the chromatography experiment, wherein the relationship is based on one or more of a peak shape, tailing factors, or a column degradation profile.

16. The computing apparatus of claim 13, wherein the new chromatography input information is third-party chromatography experiment information, and wherein the instructions further configure the apparatus to request access to the third-party chromatography experiment information from an access group, wherein the third-party chromatography experiment information is derived from chromatography experiments associated with a supply chain not under the direct supervision of an entity request a compliance analysis.

17. The computing apparatus of claim 13, wherein the instructions further configure the apparatus to apply pattern recognition to the new chromatography input information to predict a likelihood of a compliance issue that has not yet occurred.

* * * * *